(12) United States Patent
Ito et al.

(10) Patent No.: US 6,814,576 B2
(45) Date of Patent: Nov. 9, 2004

(54) ORAL CAVITY CLEANING DEVICE

(75) Inventors: Kazumasa Ito, Aichi (JP); Hiroshi Ikeda, Tokyo (JP)

(73) Assignee: Ricoh Elemex Corporation, Aichi (JP)

( * ) Notice: Subject to any disclaimer, the term of this patent is extended or adjusted under 35 U.S.C. 154(b) by 0 days.

(21) Appl. No.: 10/421,721

(22) Filed: Apr. 24, 2003

(65) Prior Publication Data

US 2003/0186189 A1 Oct. 2, 2003

Related U.S. Application Data

(62) Division of application No. 09/830,135, filed as application No. PCT/JP99/01380 on Mar. 19, 1999, now Pat. No. 6,659,768.

(30) Foreign Application Priority Data

Oct. 30, 1998 (JP) ............................................ 10-310123

(51) Int. Cl.[7] .......................... A61C 17/00; A61C 17/02
(52) U.S. Cl. .......................... 433/80; 433/91; 601/161; 15/322
(58) Field of Search .............................. 433/80, 82, 91, 433/93, 94, 95, 96; 601/161, 162, 163, 164, 165; 15/322

(56) References Cited

U.S. PATENT DOCUMENTS

| | | | | |
|---|---|---|---|---|
| 2,285,865 A | * | 6/1942 | Lowe et al. ............... | 15/24 |
| 3,520,300 A | * | 7/1970 | Flower, Jr. ................ | 433/91 |
| 3,783,473 A | * | 1/1974 | Engquist ................... | 15/322 |
| 4,655,197 A | | 4/1987 | Atkinson .................. | 601/161 |
| 5,062,413 A | * | 11/1991 | Bullard ..................... | 601/162 |
| 5,458,563 A | * | 10/1995 | Stewart ..................... | 601/162 |
| 5,573,398 A | * | 11/1996 | Towle et al. .............. | 433/80 |
| 5,891,014 A | | 4/1999 | Akiba ....................... | 600/158 |
| 6,129,547 A | * | 10/2000 | Cise et al. ................. | 433/80 |

FOREIGN PATENT DOCUMENTS

| | | |
|---|---|---|
| JP | 46-4234 | 2/1971 |
| JP | 47-26555 | 8/1972 |
| JP | 50-52792 | 5/1975 |
| JP | 56-39009 | 4/1981 |
| JP | 56-158221 | 11/1981 |
| JP | 2-37179 | 8/1990 |
| JP | 2-311624 | 12/1990 |
| JP | 6-504921 | 6/1994 |
| JP | 9-201233 | 8/1997 |
| JP | 10-33570 | 2/1998 |
| JP | 10-113231 | 5/1998 |
| JP | 10-248859 | 9/1998 |

* cited by examiner

Primary Examiner—John J Wilson
(74) Attorney, Agent, or Firm—Smith, Gambrell & Russell, LLP

(57) ABSTRACT

An oral cavity cleaning device including a cleaning head having a liquid feed port and a waste port, a liquid feed passage connected to the liquid feed port through which liquid is fed, via a pump, to the cleaning head and into the oral cavity via the liquid feed port to wash the oral cavity, a waste passage connected to the waste port through which waste liquid in the oral cavity sucked and drained in the cleaning head, and a cleaning member mounted on the cleaning head covering the liquid feed port and the waste port, the cleaning member being made of a porous material having liquid-permeating property. The cleaning member is substantially cylindrical in shape and includes a hole into which the cleaning head is removably inserted.

5 Claims, 12 Drawing Sheets

F I G. 1
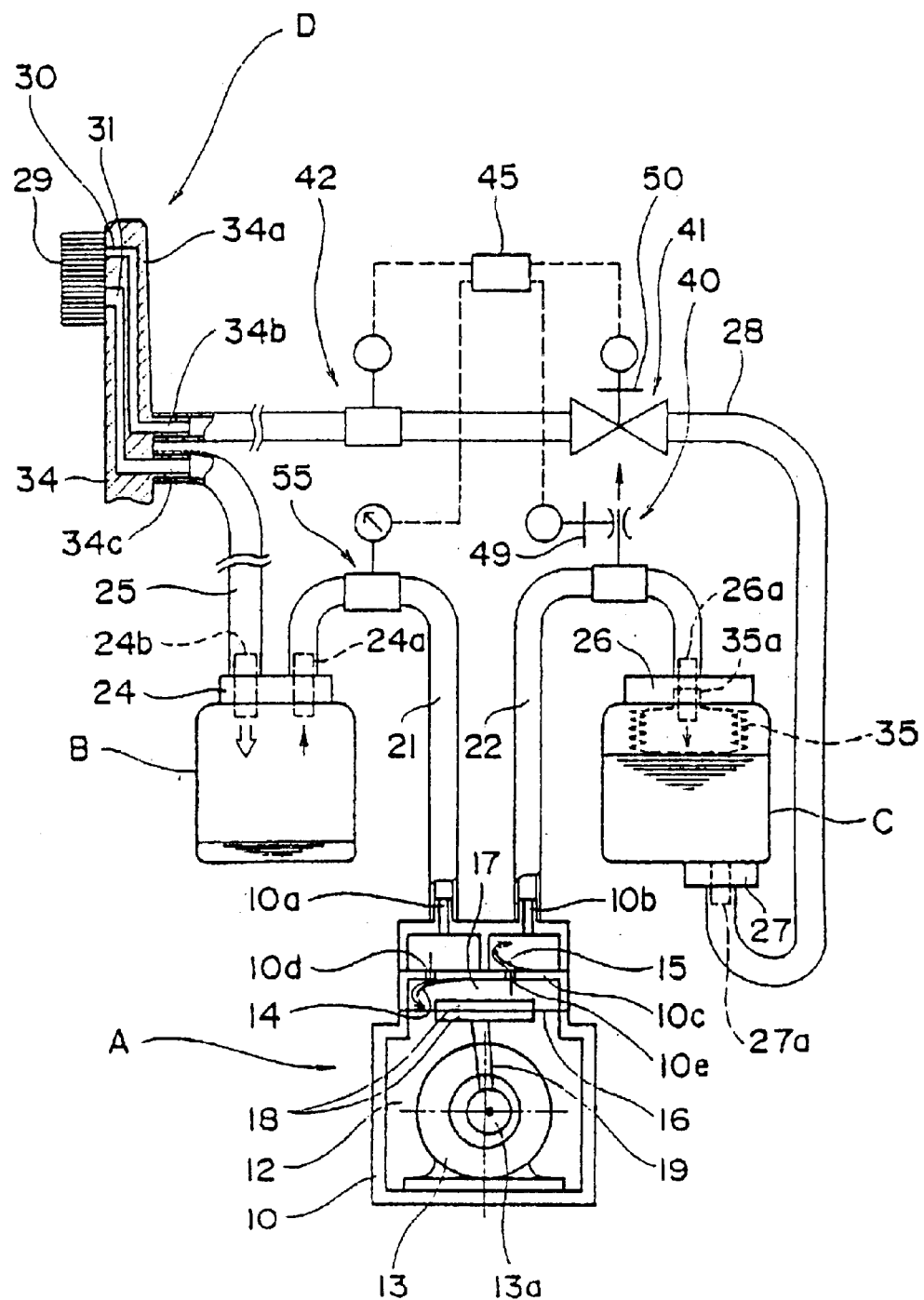

F I G. 4
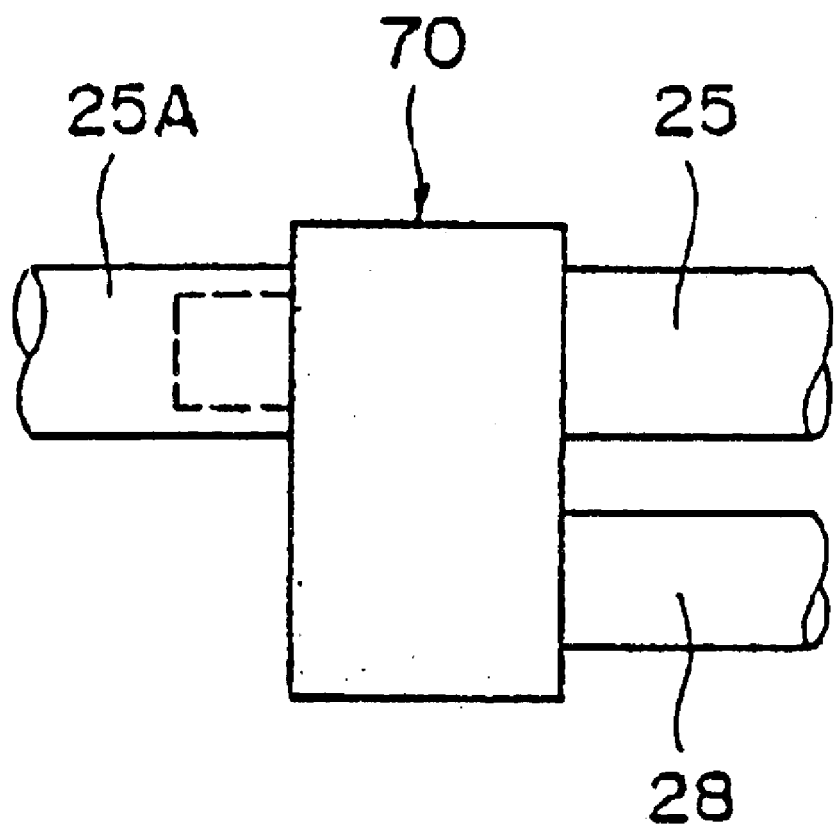

ORAL CAVITY CLEANING DEVICE

CROSS REFERENCE TO RELATED APPLICATION

This application is a division of Ser. No. 09/830,135, filed Apr. 24, 2001, now U.S. Pat. No. 6,659,768, which is a 371 national stage filing of PCT/JP99/01380 filed Mar. 19, 1999, which are being incorporated in their entirety herein by reference.

TECHNICAL FIELD

The present invention relates to an oral cavity cleaning device for cleaning the oral cavity by driving a pump with a cleaning head being introduced into the oral cavity, in order to suck the residual matter in the oral cavity, to wash the oral cavity by blowing a liquid from the cleaning head, and to suck and remove the waste liquid in the oral cavity after having washed the oral cavity.

BACKGROUND ART

There have heretofore been proposed oral cavity cleaning devices of this kind, in which a pump and a cleaning head are coupled together through a waste tube which is provided with a waste tank on its way, and the pump is driven with the cleaning head being introduced into the oral cavity to suck residual matter in the oral cavity and to drain it into the waste tank, thereby to clean the oral cavity.

According to the oral cavity cleaning device of this kind as shown, for example, in FIG. 14, the cleaning head 1 is formed in the shape of a toothbrush, a shank 2 thereof includes a slender liquid feed passage 3 and a slender waste passage 4 that run in parallel therein, and a liquid feed port 5 and a waste port 6, which are communicated with the liquid feed passage 3 and with the waste passage 4, are formed in a hair-implanted surface 2a of the brush 7.

A nursing person who attempts to wash the oral cavity of a physically handicapped person holds the cleaning head 1 by his hand to put the brush 7 into the oral cavity, and drives the pump, whereby the water stored in, for example, a liquid feed tank is sent through the liquid feed tube, supplied into the oral cavity from the liquid feed port 5 through the liquid feed passage 3 connected to the liquid feed tube while brushing the oral cavity with the brush 7, so that the brushed lees are washed away with water. The waste liquid that collects in the oral cavity is sucked by the pump from the waste port through the waste passage 4, and is drained, for example, into the waste tank through the waste tube connected to the waste passage 4.

With the above oral cavity cleaning device, however, the opening at the end of the cleaning head must have a size which is large to some extent so as to suck even those residual matters that are large to a slight degree. Then, it becomes necessary to employ a large pump to reliably suck the residual matter. An increase in the pump not only causes an increase in the cost but also causes the device as a whole to become heavy and bulky.

With the oral cavity cleaning device using the cleaning head 1 shown in FIG. 14, further, the air around the brush 7 is sucked at the time of sucking the waste liquid; i.e., the waste liquid is sucked poorly efficiently. To enhance the sucking efficiency, therefore, it becomes necessary to employ a relatively large pump similarly causing an increase in the cost and causing the whole device to become heavy and bulky. The device becomes less suited for being carried, loses operability, and gives an increased burden for a nursing person who takes care of a physically handicapped person in his home or visiting the handicapped person's home.

The object of the present invention, therefore, is to provide a device which is capable of reliably sucking the residual matter, which is cheaply constructed as a result of using a small pump, which as a whole is light in weight and small in size, which is easy to carry and easy to operate giving reduced burden for a nursing person by solving the above-mentioned problems inherent in the prior art.

DISCLOSURE OF THE INVENTION

A first invention is concerned with an oral cavity cleaning device wherein a pump is driven with a cleaning head introduced in the oral cavity to suck the residual matter in the oral cavity and to drain it into a waste liquid tank in order to clean the oral cavity, and wherein squeezing means is provided in a waste flow passage of from an end of the cleaning head to a suction port of the waste liquid tank to squeeze said waste flow passage to increase a negative pressure on the downstream of the squeezing position and, then, to suck the residual matter at a breath with the increased negative pressure by releasing the squeeze.

When the residual matter cannot be sucked with a normal suction force at the time of cleaning, the waste flow passage is squeezed by the squeezing means to increase the negative pressure on the downstream of the squeezing position and, then, the squeeze is released, so that the residual matter is sucked at a breath with the increased negative pressure.

Thus, the device as a whole is fabricated light in weight and small in size and at a reduced cost as a result of using a small pump, the device being easily carried and easily operated, giving reduced burden for the nursing person. When the residual matter cannot be sucked with the normal suction force during the cleaning, the waste flow passage is squeezed by the squeezing means to increase the negative pressure on the downstream of the squeezing position and, then, the squeeze is released, so that the residual matter is sucked at a breath with the increased negative pressure. Thus, the residual matter is reliably sucked.

In the oral cavity cleaning device of the first invention, the squeezing means may be so constituted as to compress a flexible portion of the waste tube. The flexible portion of the waste tube is compressed by the squeezing means to squeeze the waste flow passage. Thereafter, compression is released to open the waste flow passage. This makes it possible to improve the operability of the squeezing means relying upon a simple and cheap constitution in addition to obtaining the effect of the first invention.

In the oral cavity cleaning device of the first invention, further, the squeezing means may be so constituted as to open and close the end of the cleaning head. Then, the end of the cleaning head is closed by the squeezing means to squeeze the waste flow passage. Thereafter, the end of the cleaning head is opened to open the waste flow passage. This similarly makes it possible to increase the degree of vacuum up to the end of the cleaning head to improve the sucking efficiency in addition to obtaining the effect of the first invention.

In the oral cavity cleaning device of the first invention, further, the squeezing means may be constituted by a hand switch and a valve which electrically opens and closes the waste flow passage upon operating the hand switch. The hand switch is operated to close the valve and, hence, to squeeze the waste flow passage. Thereafter, the valve is opened to open the waste flow passage. Since the valve is opened and closed by turning the hand switch on or off, the squeezing means is more easily operated with a light touch in addition to obtaining the effect of the first invention.

In the oral cavity cleaning device of the first invention, further, the squeezing means may be operated at regular time intervals when the pump is driven to squeeze the waste flow passage. When the pump is driven, therefore, the squeezing means is automatically operated at regular time intervals to squeeze the waste flow passage. This enhances the operability eliminating the need of operating the squeezing means by hand each time in addition to obtaining the effect of the first invention.

A second invention is concerned with an oral cavity cleaning device wherein a pump is driven with a cleaning head introduced in the oral cavity to suck the residual matter in the oral cavity and to drain it into a waste liquid tank in order to clean the oral cavity, and wherein a water feed port of a water feed tube is provided in a waste flow passage of from an end of the cleaning head to a suction port of the waste liquid tank to increase the negative pressure in said waste flow passage by feeding water through the water feed tube and, then, to suck the residual matter at a breath with the increased negative pressure by no longer feeding the water.

When residual matter cannot be sucked with the normal suction force at the time of cleaning, the water is supplied to the waste flow passage from the water feed port through the water feed tube to increase the negative pressure in the waste flow passage, so that the residual matter is sucked at a breath with the increased negative pressure.

When the residual matter cannot be sucked with the normal suction force at the time of cleaning, therefore, the water is supplied into the waste flow passage from the water feed port through the water feed tube to increase the negative pressure in the waste flow passage, so that the residual matter is sucked at a breath with the increased negative pressure. Even when the amount of residual matter is small, therefore, the residual matter can be reliably sucked together with the water.

A third invention is concerned with an oral cavity cleaning device wherein a pump is driven to feed a liquid into the oral cavity through a liquid feed passage in a cleaning head to wash the oral cavity, and the waste liquid in the oral cavity is sucked and is drained through a waste passage in the cleaning head, and wherein a cleaning member is mounted on the cleaning head covering the liquid feed port and the waste port, the cleaning member being made of a porous material such as a sponge having a liquid-permeating property.

At the time of cleaning the oral cavity, the cleaning member is fitted to a portion to be cleaned in the oral cavity, and the waste liquid is sucked through the cleaning member.

At the time of sucking the waste liquid in the oral cavity by the pump, therefore, the cleaning member limits the suction of the air and, besides, the waste liquid is sucked through the cleaning member. This helps increase the ability for sucking the waste liquid, enabling the pump of a small size to be employed. Accordingly, the oral cavity cleaning device as a whole is constructed in a compact size and at a decreased cost. Further, since the cleaning is effected with the cleaning member being impregnated with a suitable amount of liquid, even the dry oral cavity can be washed comfortably and efficiently.

In the above-mentioned oral cavity cleaning device of the third invention, the cleaning head may be replaceably provided with the cleaning member. When the cleaning member is worn out, the cleaning member is removed from the cleaning head and is replaced by a new one. This makes it possible to replace only the cleaning member that is worn out by a new one and, hence, to use the oral cavity cleaning device for an extended period of time in addition to obtaining the effect of the third invention.

The cleaning head may be provided with a waste pipe that forms a waste passage, and the end of the waste pipe may be arranged in the cleaning member. The end of the waste pipe provided for the cleaning head is disposed inside the cleaning member and does not come into direct contact with the oral cavity, enabling the device to be comfortably used in addition to obtaining the effect of the third invention.

It is further desired that the outer circumference of the cleaning member is formed rugged. At the time of washing the oral cavity, foul and dirty matters such as lees of foods are scraped off by the rugged portion of the cleaning member. Since the outer circumference of the cleaning member is formed rugged, foul and dirty matters such as lees of foods are effectively scraped off by the rugged portion at the time of cleaning the oral cavity contributing to enhancing the efficiency for washing the oral cavity in addition to obtaining the effect of the third invention.

At the time of cleaning the cleaning member, further, there may be provided a cleaning pump for feeding the liquid to the cleaning member through the waste passage. At the time of cleaning the cleaning member, the cleaning pump is driven, whereby the liquid is fed to the cleaning member through the waste passage to wash away the foul and dirty matters adhered on the cleaning member. Thus, the cleaning member is cleaned by using the waste passage and feeding the liquid to the cleaning member through the waste passage. Therefore, the cleaning member is easily and effectively washed without using tap water in addition to obtaining the effect of the third invention.

Moreover, the cleaning head may be constituted by detachably attaching a grip to a head body, forming an outer member such as an outer case of the head body using an elastic member, and fitting an end of the grip to a base end of the outer member to air-tightly couple the grip and the outer member together. The cleaning head is constituted by detachably attaching the grip to the head body in a manner that they can be disassembled. It is therefore allowed to easily clean the head. Besides, the outer member of the cleaning head is made of an elastic member, and the outer member itself is air-tightly coupled to the grip, making it possible to decrease the number of parts and to decrease the cost.

BRIEF DESCRIPTION OF THE DRAWINGS

FIG. 1 is a view schematically illustrating the constitution of an oral cavity cleaning device equipped with a toothbrush;

FIG. 4 is a view illustrating the constitution of an adaptor portion used in the oral cavity cleaning device;

BEST MODE FOR CARRYING OUT THE INVENTION

Figure 2:
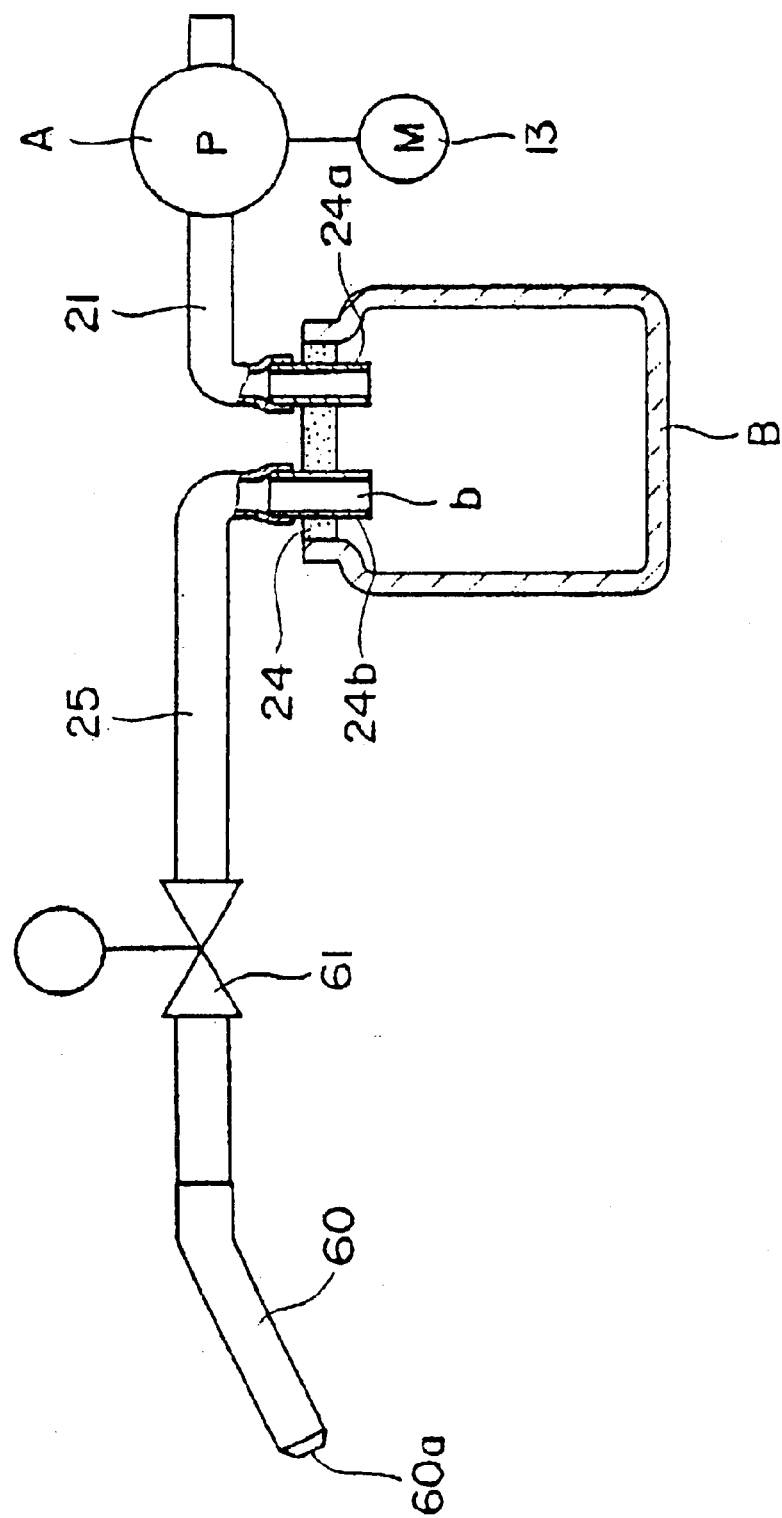
FIG. 2 is a view illustrating a basic constitution of the oral cavity cleaning device equipped with a cleaning head instead of the toothbrush.

FIG. 1 is a view schematically illustrating the constitution of an oral cavity cleaning device equipped with a toothbrush. The diagramed oral cavity cleaning device includes a pump A, a waste liquid tank B, a liquid feeding tank C and a toothbrush D.

The pump A has a suction port 10a and a blow-out port 10b formed in the top wall of a pump casing 10. The interior of the pump casing 10 is partitioned by a partitioning wall 10c, and communication holes 10d, 10e are formed in the partitioning wall 10c so as to be communicated with the suction port 10a and the blow-out port 10b. An intake valve 14 is provided so as to be freely opened and closed at a position of the communication hole 10d on the lower wall surface of the partitioning wall 10c, and a discharge valve 15 is provided so as to be freely opened and closed at a position of the communication hole 10e on the upper wall surface.

Space under the partitioning wall 10c is partitioned by a diaphragm 16 thereby to form a pump chamber 17 on the upper side and to form a motor chamber 12 on the lower side. The diaphragm 16 has membrane plates 18, 18 on both sides at the central portion thereof, and supports them to reciprocally move up and down in the drawing. An upper end of a connecting rod 19 is coupled to the lower membrane plate 18, and a lower end thereof is coupled to an eccentric cam 13a fitted to a motor 13 in the motor chamber 12.

A discharge tube 21 which is connected at its one end to the waste liquid tank B is connected at its other end to the suction port 10a of the pump A, and a discharge tube 22 connected at its one end to the liquid feeding tank C is connected at its other end to the blow-out port 10b.

The waste liquid tank B is detachably provided with a closure 24 at the port thereof. An end of the discharge tube 21 is connected to one connection tube 24a that penetrates through the closure 24. Further, a waste tube 25 connected at its one end to a toothbrush D is connected at its other end to the other connection tube 24b.

The liquid feeding tank C contains the water which is a washing liquid to be fed to the oral cavity. A pharmaceutical solution may be contained. The liquid feeding tank C is detachably provided with a closure 26 at the tank port thereof. An end of the discharge tube 22 is connected to a connection tube 26a that penetrates through the closure 26. Further, a closure 27 is detachably attached to a coupling hole in the bottom portion, and a liquid feed tube 28 is connected at its one end to the toothbrush D is connected at its other end to a connection tube 27a that penetrates through the closure 27.

A head portion 34a of a shank 34, where the brush 29 of the toothbrush D is implanted, is provided with plural liquid feed ports 30 and waste ports 31 avoiding the portions where the brush is implanted. A liquid feed tubular portion 34b and a waste tubular portion 34c are formed in the shank 34 on the side opposite to the brush 29, and are communicated with the liquid feed port 30 and the waste port 31 through separate flow passages. The liquid feed tube 28 is connected to the liquid feed tubular portion 34b and the waste tube 25 is connected to the waste tubular portion 34c.

In the above-mentioned oral cavity cleaning device, a volume-varying member 35 is provided in the liquid feeding tank C. The volume-varying member 35 undergoes the expansion and contraction depending upon the amount of the air when the air is introduced therein, and is formed in the shape of, for example, a bellows as shown in FIG. 1. It may be like, for example, a rubber balloon. The volume-varying member 35 is disposed in the liquid feeding tank C with its upwardly directed port 35a being intimately attached to the connection tube 26a.

The above-mentioned oral cavity cleaning device is equipped with a flow rate adjusting unit that adjusts the flow rate of the washing water flowing through the liquid feed tube 28 to adjust the flow rate of the washing water fed into the oral cavity, and with a flow rate detector means for detecting the flow rate thereof.

As shown in FIG. 1, for example, the flow rate adjusting unit includes a discharge valve 40 provided at the air outlet port (not shown) communicated with the discharge tube 22, and a flow rate valve 41 provided in the liquid feed tube 28. As the flow rate detector means, on the other hand, provision is made of a flow rate sensor 42 in the liquid feed tube 28 downstream of the flow rate valve 41.

The discharge valve 40, flow rate valve 41 and flow rate sensor 42 are connected to drive control means 45 through signal lines as indicated by dotted lines in the drawing. Based on the detected result of flow rate of the flow rate sensor 42, the drive control means 45 controls the opening and closure of the discharge valve 40 and of the flow rate valve 41, so that the flow rate of the washing water flowing through the liquid feed tube 28 becomes a predetermined setpoint quantity.

A nursing person who attempts to brush the teeth of physically handicapped person by using the above-mentioned oral cavity cleaning device, turns the power source switch (not shown) on to open the discharge valve 40 and the flow rate valve 41. Then, the nursing person holds the toothbrush D, inserts the head portion 34a thereof into the oral cavity of the physically handicapped person and turns the drive switch (not shown) of the pump A on to drive the motor 13. Then, the diaphragm 16 reciprocally moves to repeat the suction and discharge; i.e., the intake valve 14 is opened enabling the air to be taken in the pump chamber 17 through the suction port 10a, and the discharge valve 15 is opened to blow out the air from the pump chamber 17 through the blow-out port 10b.

The air blown out from the blow-out port 10b is fed into the volume-varying member 35 through the discharge tube 22 thereby to inflate the volume-varying member 35 and to push the washing water in the liquid feeding tank C, to push the water out into the liquid feed tube 28 from the liquid feeding tank C, and to feed the water into the oral cavity from the liquid feed port 30 of the toothbrush D through the liquid feed tube 28. The oral cavity is washed out with the washing water.

To drain the waste liquid collected in the oral cavity, the brush 29 is suitably fitted to a portion where there is collected the waste liquid. Owing to the sucking action of the pump A, the waste liquid is sucked through the waste port 31 and is drained into the waste liquid tank B through the waste tube 25.

At the time of brushing the teeth, the flow rate of the washing water flowing through the liquid feed tube 28 is detected by the flow rate sensor 42. When the present flow rate detected by the flow rate sensor 42 is not in agreement with the flow rate that has been set in advance by the drive control means 45, the flow rate valve 41 is suitably opened and closed by the drive control means 45, so that the present flow rate becomes equal to the setpoint quantity.

In adjusting the flow rate, however, when the setpoint quantity is not reached despite the flow rate valve 41 is opened to its maximum degree, the discharge valve 40 is closed by the drive control means 45 to squeeze the amount of the air discharged to the outside from the air outlet port thereby to increase the amount of the air fed into the volume-varying member 35. Thus, the flow rate of the washing water flowing through the liquid feed tube 28 is increased to reach the setpoint quantity.

In the foregoing description, the flow rate of the washing water flowing through the liquid feed tube 28 was automatically adjusted by the drive control means 45 to become equal to the setpoint quantity. It is, however, also allowable to open or close the discharge valve 40 or the flow rate valve 41 of the flow rate adjusting unit by hand to adjust the flow rate of the washing water flowing through the liquid feed tube 28 to become any desired amount.

As shown in, for example, FIG. 1, a manual adjustment knob 49 for opening and closing the discharge valve 40 and a manual adjustment knob 50 for opening and closing the flow rate valve 41, are provided in a manner that they can be operated from the outside.

When the nursing person wishes to adjust the flow rate of the washing water fed into the oral cavity of the physically handicapped person in brushing the teeth, he depresses the change-over switch to change the drive control means 45 over to a manual mode. Then, the nursing person operates the manual adjustment knob 50 to open or close the flow rate valve 41 while seeing the interior of the oral cavity to adjust the flow rate of the washing water flowing through the liquid feed tube 28 to become a desired amount. Thereafter, the nursing person turns the manual adjustment completion switch on, and the desired flow rate detected by the flow rate sensor 42 is stored in the drive control means 45. Then, the flow rate valve 41 is suitably opened or closed by the drive control means 45 depending upon the result of flow rate detected by the flow rate sensor 42, so that the above-mentioned desired amount is maintained.

When the desired flow rate is not reached by the adjustment by opening and closing the flow rate valve 41, the manual adjustment knob 49 is operated to open or close the discharge valve 40, in order to increase the flow rate of the washing water fed into the liquid feed tube 28 so as to reach the setpoint quantity.

The above-mentioned oral cavity cleaning device is provided with a pressure sensor 55 for detecting the pressure in the discharge tube 21. The pressure sensor 55 is connected to the drive control means 45 through a signal line as indicated by a dotted line in FIG. 1, and the flow rate valve 41 is closed by the drive control means 45 when the pressure detected by the pressure sensor 55 lies outside a predetermined range. Reception of an electric signal from the pressure sensor 55 by the drive control means 45 takes a precedence over reception of an electric signal from the flow rate sensor 42 by the drive control means 45 at the time of adjusting the flow rate.

In brushing the teeth, it may often happen, depending upon the condition of use, that the waste tube 25 is clogged with foreign matter to a degree that the tube is not completely blocked causing the negative pressure to become too large, or that the waste tube 25 is pierced causing the negative pressure to become too small. In such a case, the washing water is fed, though not in so large amounts, into the oral cavity while the waste liquid in the oral cavity is not sucked to a sufficient degree, and, hence, the waste liquid in the oral cavity may just become to overflow.

According to this embodiment, therefore, when the pressure detected by the pressure sensor 55 lies outside the predetermined range, the flow rate valve 41 is closed by the drive control means 45 to discontinue the supply of washing water into the oral cavity, so that the waste liquid will not be collected any more in the oral cavity. When foreign matter is removed from the waste tube 25 and the pressure returns to normal, the waste liquid in the oral cavity is sucked and is drained into the waste liquid tank B.

In the oral cavity cleaning device, the waste tube 25 that is shown can be entirely or partly replaced by a waste tube having a cleaning head at an end thereof and a squeezing means on its way.

FIG. 2 illustrates a basic constitution of the oral cavity cleaning device that is equipped with the cleaning head instead of the toothbrush. In FIG. 2, symbols A, B, 13 and 21 denote the pump, waste liquid tank, motor and discharge tube shown in FIG. 1. Further, reference numeral 24 denotes the closure, 24a denotes the one connection tube, and 24b denotes the other connection tube. Reference numeral 25 denotes the waste tube shown in FIG. 1, or a new waste tube that is replaced. A cleaning head 60 is attached to an end of the waste tube 25, and a squeezing means 61 is provided on the way. Thus, squeezing means 61 for squeezing the waste flow passage is provided in the waste flow passage of from the end 60a of the cleaning head 60 up to the suction port b of the waste liquid tank B.

To use the device, the cleaning head 60 is introduced into the oral cavity and the pump A is driven, in order to clean the oral-cavity by sucking residual matter such as lees of foods staying in the oral cavity and draining the residual matter into the waste liquid tank. B.

In effecting the cleaning, when the residual matter cannot be sucked with the normal suction force, the waste flow passage is squeezed by using the squeezing means 61 to increase the negative pressure in the waste liquid tank B, in the discharge tube 21 and in the waste tube 25. Thereafter, the squeeze is released to suck the residual matter at a breath with an increased negative pressure.

The degree of vacuum can be quickly increased if the waste flow passage is completely squeezed or closed by the squeezing means 61. The waste flow passage, however, may not be completely squeezed.

Figure 3:
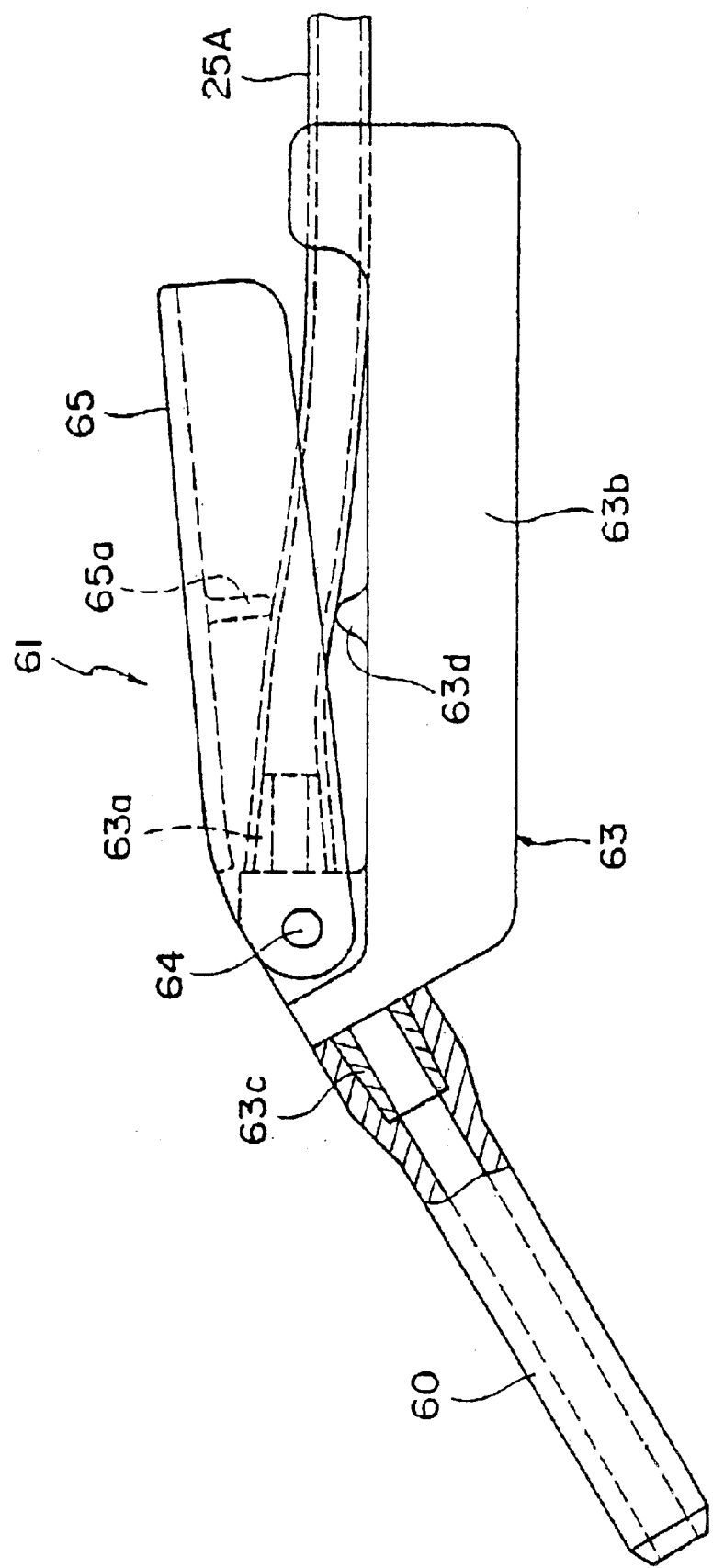
FIG. 3 is a view illustrating, in a partly cut-away manner, the constitution of squeezing means used in the oral cavity cleaning device.

FIG. 3 illustrates the squeezing means 61. In this example, the waste tube 25A is a flexible tube and its end is connected to one connection tubular portion 63a of a holder 63. The holder 63 has, at an end of a grip portion 63b, the other connection tubular portion 63c that is communicated with the one connection tubular portion 63a and is protruding in the opposite direction. A base end of the cleaning head 60 is attached to the other connection tubular portion 63c. A waste flow passage is formed from the cleaning head 60 to the waste tube 25A through the holder 63.

A lever 65 is mounted on the holder 63 so as to rotate with a support shaft 64 as a center. The lever 65 is provided with a protuberance 65a, and the holder 63, too, is provided with a protuberance 63d being opposed to the protuberance 65a with the waste tube 25A sandwiched therebetween.

To use the device, the grip portion 63b and the lever 65 are held by one hand, the cleaning head 60 is introduced into the oral cavity, and the pump A is driven. To intensify the suction force, the lever 65 is suitably strongly gripped and turned to compress the flexible portion of the waste tube 25A between the protuberances 65a and 63a in order to squeeze the waste flow passage. Thereafter, the hand is loosened to return the lever 65; i.e., the waste tube 25A is no longer compressed, the waste flow passage is opened, and the residual matter in the oral cavity is sucked at a breath with the increased negative pressure.

In the example shown in FIG. 3, the other end of the waste tube 25A is connected to an adaptor 70 as shown in FIG. 4. To the adaptor 70 are connected the waste tube 25 and the liquid feed tube 28 shown in FIG. 1. The waste tubes 25A and 25 are connected through the adaptor 70, but the opening at an end of the liquid feed tube 28 is closed by the adaptor 70.

Figure 5:
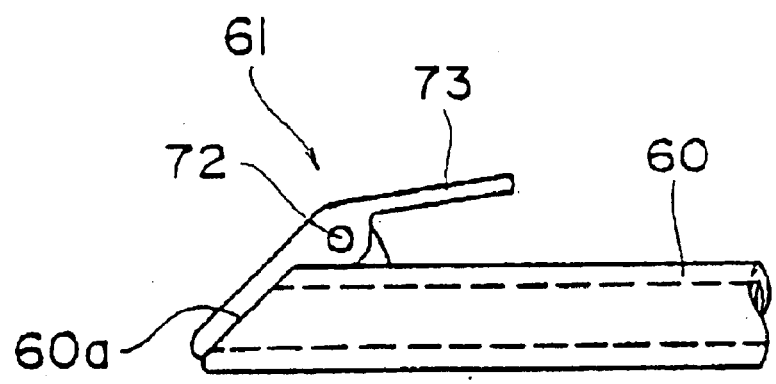
FIG. 5 is a view illustrating the constitution of another squeezing means.

FIG. 5 illustrates another example of the squeezing means 61. This example is provided with an open/close closure 73 that turns about a fulcrum 72 to open and close the end 60a of the cleaning head 60. Normally, the open/close closure 73 is opened. To intensify the suction force, the end 60a of the cleaning head 60 is closed as shown to squeeze the waste flow passage. Thereafter, the open/close closure 73 is opened to no longer squeeze the waste flow passage, whereby the residual matter in the oral cavity is sucked at a breath with an increased negative pressure.

In the example shown in FIG. 5, the open/close closure 73 is opened and closed by being turned. However, the opening at the end of the cleaning head 60 may be opened and closed by being slid. Thus, the suction force of the cleaning head 60 can be adjusted according to the degree of squeezing of the opening at the end.

Figure 6:
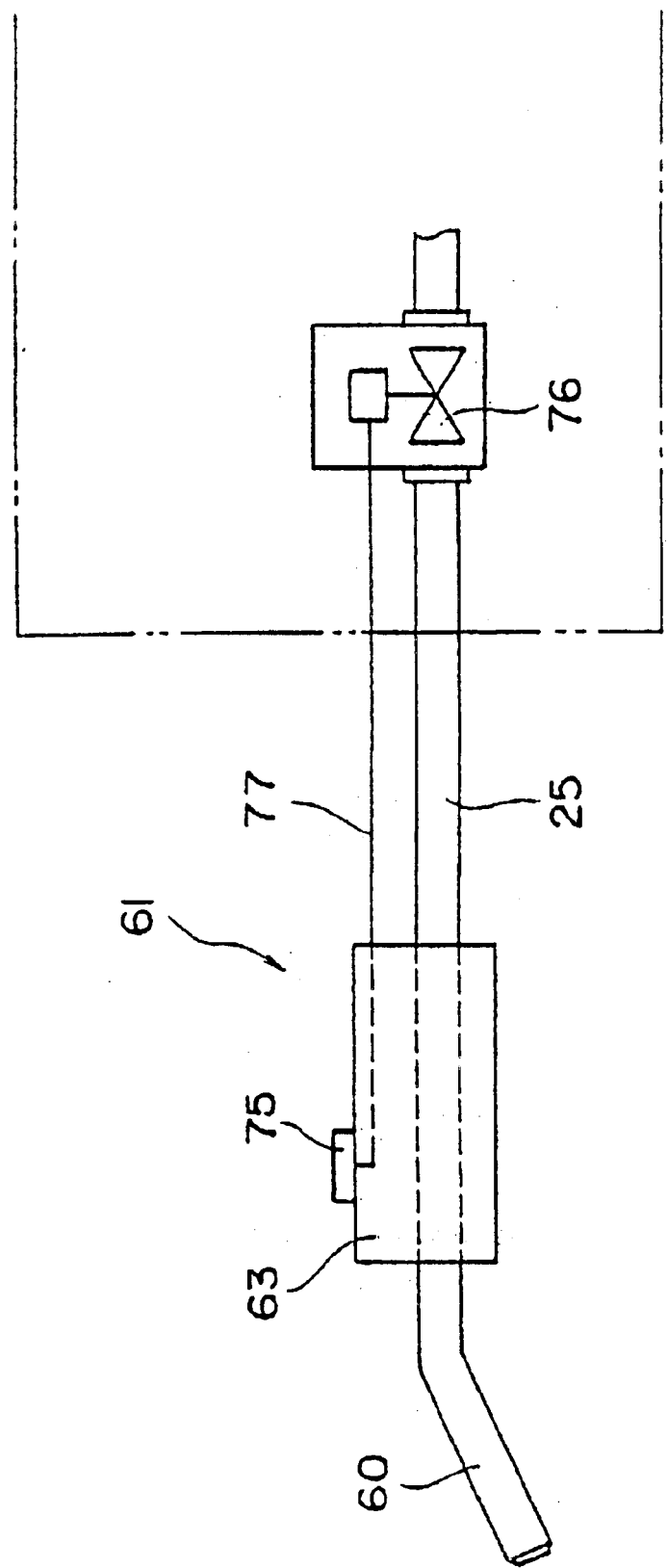
FIG. 6 is a view illustrating the constitution of a further squeezing means.

FIG. 6 illustrates a further example of the squeezing means 61. In this example, the holder 63 holding the cleaning head 60 is provided with a hand switch 75 such as a touch switch or a rubber switch that is turned on or off with a light touch operation, and with a valve 76 such as an electromagnetic valve that electrically opens and closes the waste flow passage upon the on/off operation, the switch 75 and the valve 76 being connected together through a signal line 77.

The hand switch 75 is turned on to close the valve 76 in order to squeeze the waste flow passage. Then, the hand switch 75 is turned off to open the valve 76, so that the residual matter in the oral cavity is sucked at a breath with the increased negative pressure.

In the above-mentioned examples, the squeezing means 61 was opened and closed all by hand. When the pump A is being driven, however, the squeezing means 61 may be automatically operated at regular time intervals to squeeze the waste flow passage.

Figure 7:
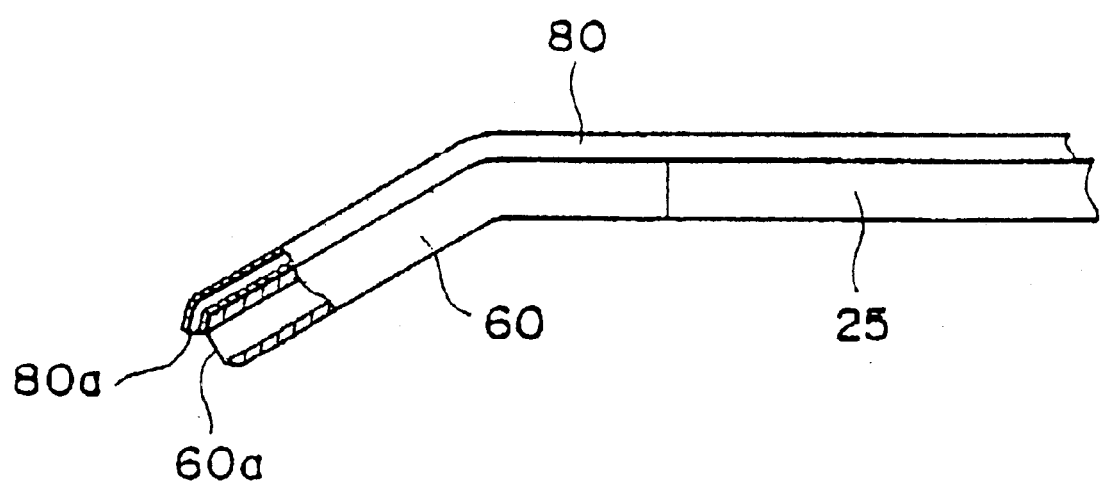
FIG. 7 is a view illustrating, in a partly cut-away manner, another oral cavity cleaning device equipped with the cleaning head.

FIG. 7 illustrates a further embodiment of the oral cavity cleaning device equipped with the cleaning head. In this embodiment, a water feed tube 80 is provided along the waste tube 25 and along the cleaning head 60 at the end thereof The water feed tube 80 is connected to the liquid feed tube 28 via, for example, an adaptor as shown in FIG. 1. A water feed port 80a at the end is headed toward an end 60a of the cleaning head 60.

When the residual matter cannot be sucked with the normal suction force during the cleaning, the water is fed from the water feed port 80a into the waste flow passage through the water feed tube 80 in order to increase the negative pressure in the waste tube 25, and the residual matter is sucked at a breath with the increased negative pressure.

In the diagramed embodiment, the water feed port 80a of the water feed tube 80 is directed to the end of the cleaning head 60. Not being limited to the end, however, the water feed port 80a may be provided being directed to the waste flow passage of up to the suction port b of the waste liquid tank B.

Figure 8:
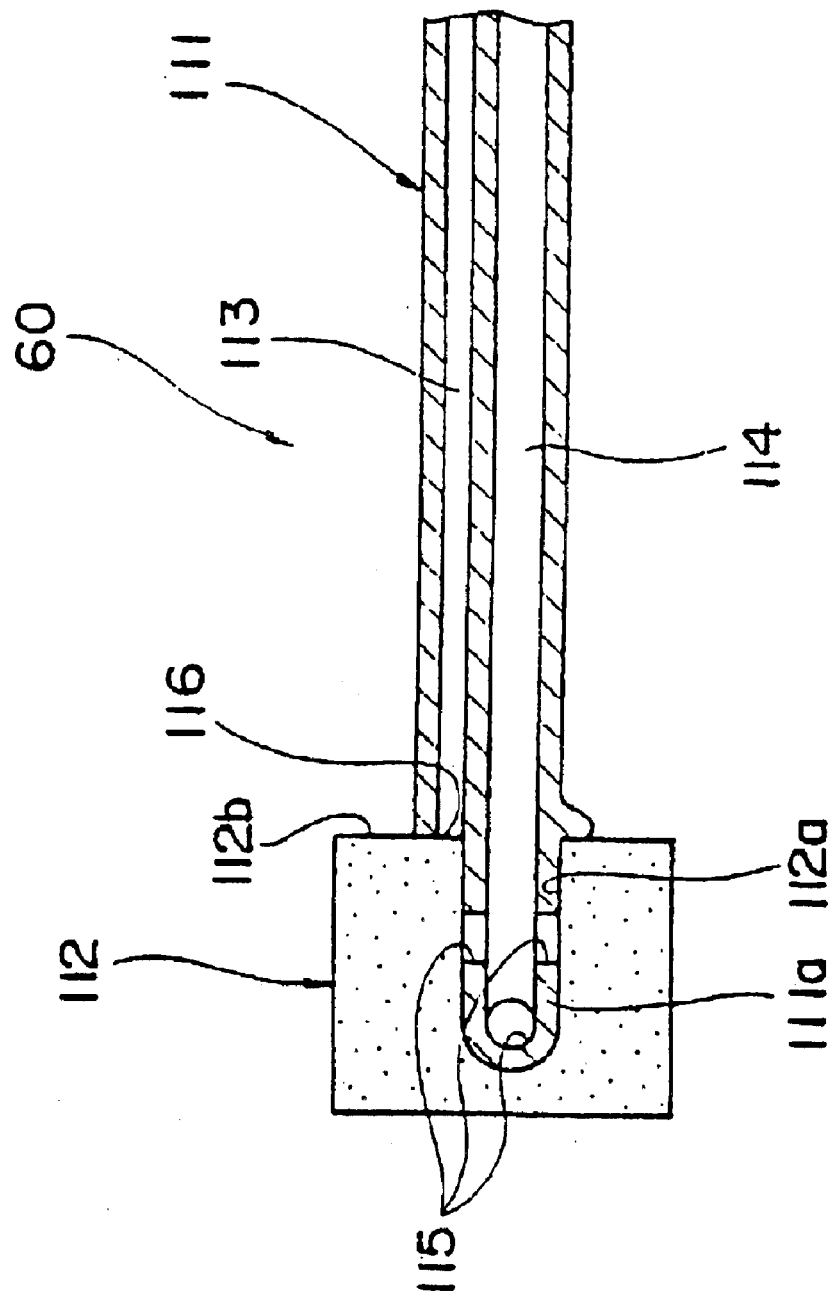
FIG. 8 is a sectional view illustrating, in a partly omitted manner, another cleaning head that is attached instead of the toothbrush.

FIG. 8 illustrates a still further example of the cleaning head attached instead of the toothbrush. The cleaning head 60 has a cleaning member 112 attached to the end of a slender shank 111.

The shank 111 is made of, for example, a resin and has a liquid feed passage 113 and a waste passage 114 penetrating therein in the lengthwise direction and separated from each other, the waste passage 114 protruding longer than the liquid feed passage 113. Plural waste ports 115 are provided in the outer periphery of an end protruded portion 111a of the shank 111, and a liquid feed port 116 is opened in a direction in which the end protruded portion 111a protrudes. Though not shown, the waste tube 25 shown in FIG. 1 is connected to the base end side of the shank 111, and the liquid feed tube 28 is also connected thereto.

The cleaning member 112 is made of a porous material having liquid-permeating property, such as a foamed material like sponge, and has a hole 112a. It is desired that the sponge used as the cleaning member 112 has a foaming density of from 30 to 80 kg/m$^3$ and a foamed particle diameter of from 0.5 to 1.0 mm. It is further allowable to use a cloth or a felt provided it is porous and has liquid-permeating property. The end protruded portion 111a is inserted in the hole 112a, the cleaning member 112 is adhered to the shank 111, and the liquid feed port 116 is pushed onto the rear end surface 112b of the cleaning member 112.

When the nursing person uses the oral cavity cleaning device to wash the oral cavity of the physically handicapped person, he holds' the shank 111 by hand and introduces the cleaning member 112 into the oral cavity of the physically handicapped person.

Then, the pump A shown in FIG. 1 is driven to introduce the water from the liquid feed tank C into the liquid feed passage 113 through the liquid feed tube 28 and to send the water into the oral cavity from the liquid feed port 116 through the liquid feed passage 113 and the cleaning member 112. Then, the oral cavity is washed with the cleaning member 112 impregnated with water. Here, it is also allowable to use a liquid such as a pharmaceutical solution other than the water.

When the waste liquid and brushed lees are collected in the oral cavity, the cleaning member 112 is fitted to a portion to be cleaned, the waste liquid is sucked through the cleaning member 112, and is further sucked from the waste port 115 through the waste passage 114, and is drained into the waste liquid tank B through the waste tube 25 shown in FIG. 1. The brushed lees and the like that do not pass through the cleaning member 112 are adsorbed by the surface of the cleaning member 112 and are removed from the oral cavity.

After the oral cavity is washed, the cleaning member 112 is washed with, for example, water to remove the brushed lees attached clean from the surfaces thereof.

In the above-mentioned oral cavity cleaning device, the cleaning member 112 may be cleaned by feeding the water through the water passage 114 of a diameter larger than that of the liquid feed passage 113.

Therefore, though not diagramed, a cleaning pump is provided in addition to the above-mentioned pump A for feeding the liquid, and is connected to the waste passage 114 through another tube. At the time of cleaning the cleaning member 112, the pump A is halted, and the water is fed by the cleaning pump through the waste passage 114 to wash the cleaning member 112.

In this case, the pump A, too, may be driven, to feed the water through two flow passages, i.e., through the waste passage 114 and the liquid feed passage 113. It is further allowable not to provide the cleaning pump. Namely, at the time of cleaning the cleaning member 112, the flow passage is changed over by, for example, flow passage change-over means, the first pump A for feeding the liquid is driven to introduce the water into the waste passage 114 and, hence, to send the water to the washing member 112.

In the above-mentioned oral cavity cleaning device, it is desired that the cleaning member 112 has its outer circumference formed rugged in order to easily scrape off foul and dirty matter in the oral cavity.

Figure 9:
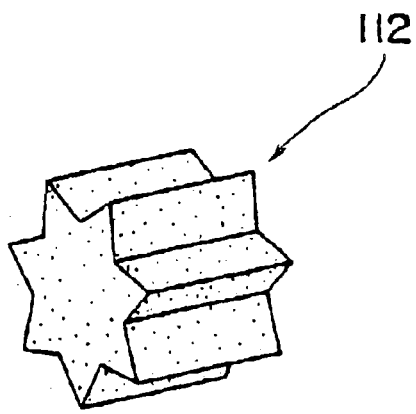
FIG. 9 is a perspective view illustrating a cleaning member of the cleaning head.
Figure 10:
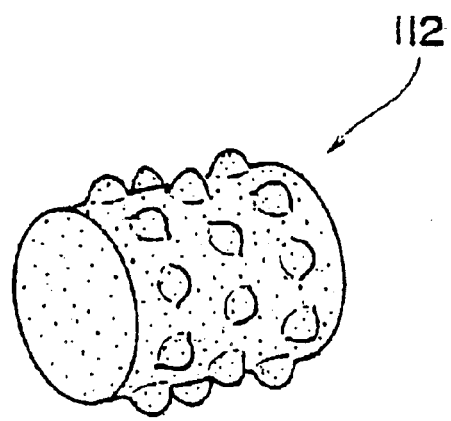
FIG. 10 is a perspective view illustrating another example thereof.
Figure 11:
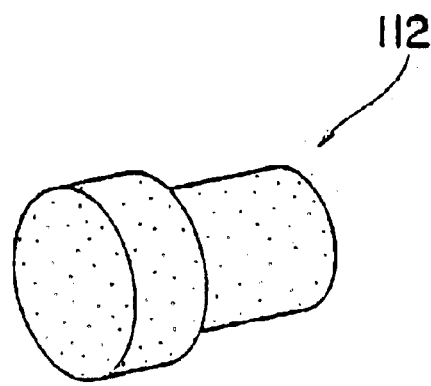
FIG. 11 is a perspective view illustrating a further example thereof.

For this purpose, it is desired to use the cleaning member 112 of a star shape in cross section as shown in FIG. 9, of a shape having many protuberances on the outer periphery thereof as shown in FIG. 10, and of a shape having a step in the outer periphery as shown in FIG. 11.

Figure 12:
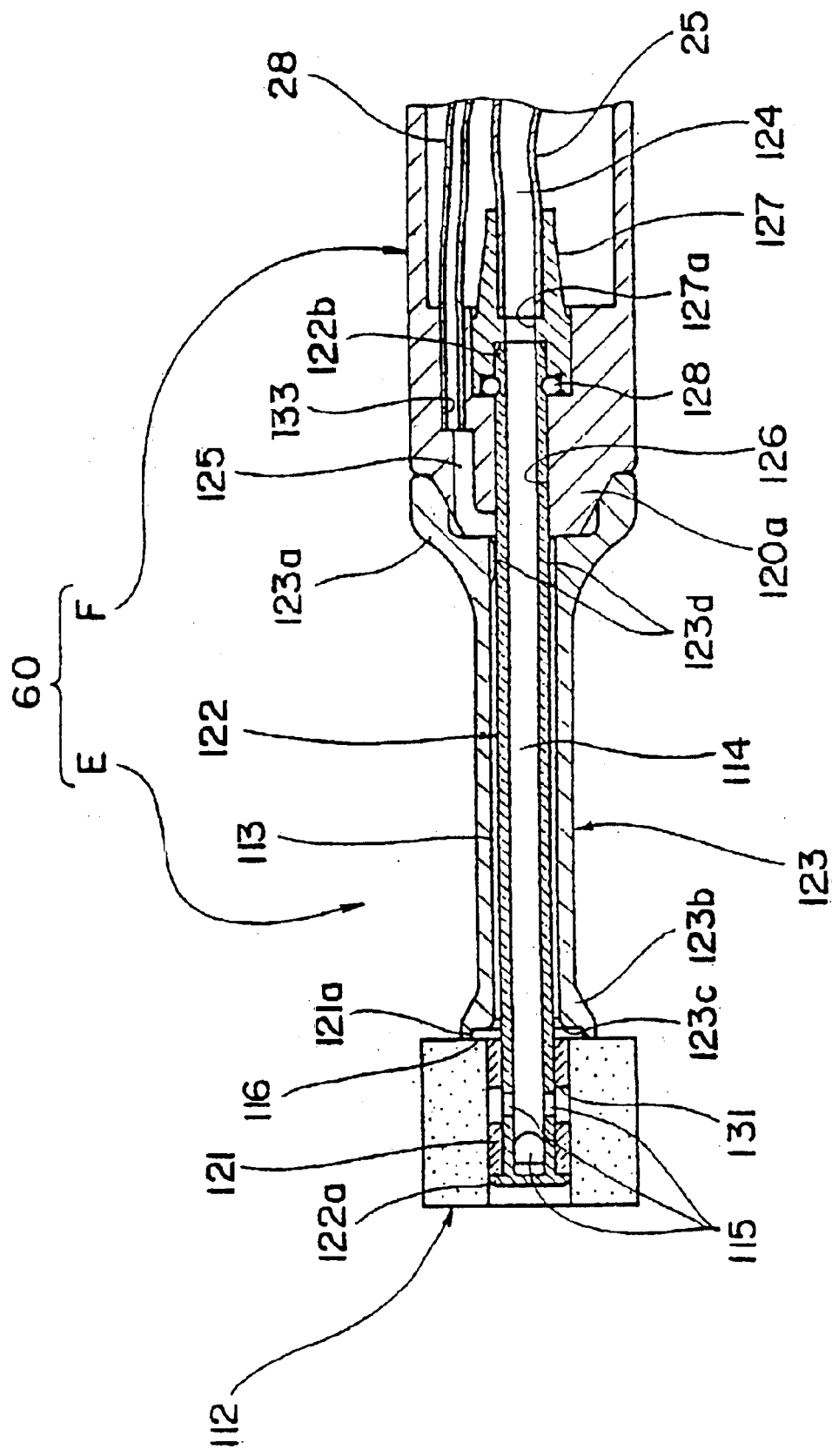
FIG. 12 is a sectional view illustrating, in a partly omitted manner, another cleaning head provided for the oral cavity cleaning device according to the invention.
Figure 13:
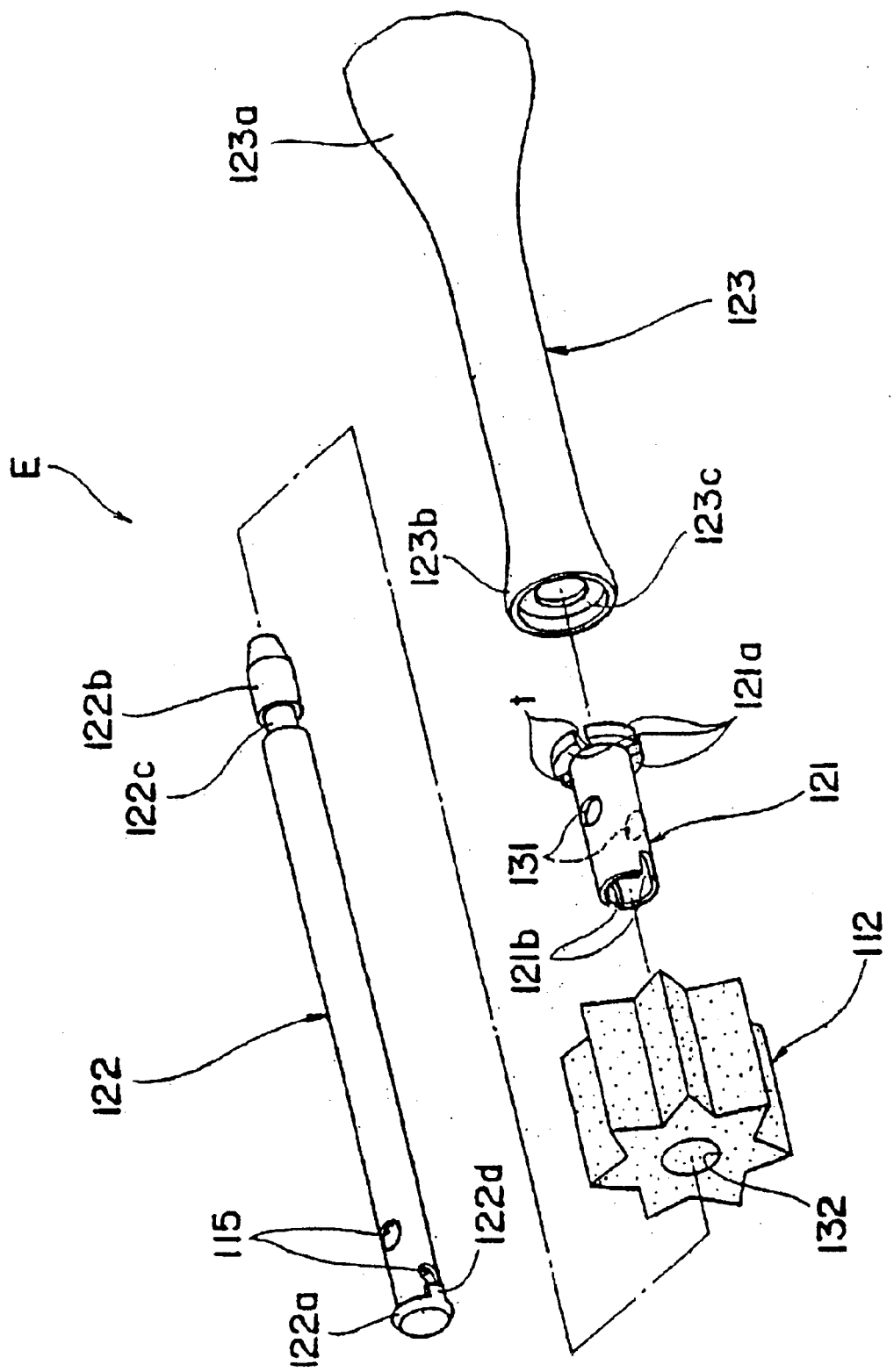
FIG. 13 is a perspective view illustrating the head body of the cleaning head in a disassembled manner.
Figure 14:
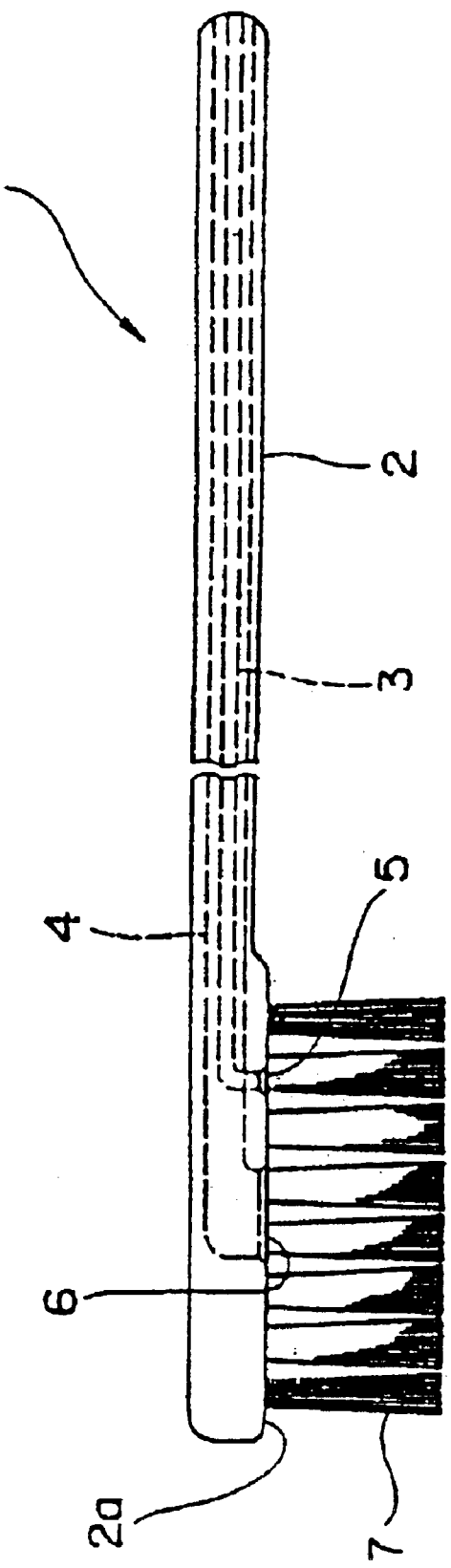
FIG. 14 is a side view illustrating a cleaning head of a conventional oral cavity cleaning device.

In the present invention, the cleaning head 60 can be constituted as shown, for example, in FIGS. 12 and 13.

The cleaning head 60 is constituted by a head body E and a grip F. The head body E includes the cleaning member 112 of a star shape in cross section, a sleeve 121 for mounting the cleaning member 112, a waste pipe designated at 122, and an outer casing designated at 123.

FIG. 12 shows the front end side of the grip F in a partly omitted manner. The grip F as a whole is of a slender cylindrical shape having a front end 120a that is gradually narrowed toward the end. The front end 120a has a fitting hole 126 that penetrates through near the center thereof and further has another fitting hole 133 on the upper side of the fitting hole 126 and is smaller than the fitting hole 126, thereby to form a flow passage 125.

The fitting hole 126 has a large diameter on the right side in the drawing, and a cylindrical coupling member 127 is fitted and secured thereto. The coupling member 127 has an annular protuberance 127a on the inner circumference nearly at the center thereof, and has a circumferential groove formed in the left end in the drawing and in which an O-ring 128 is fitted. An end of the waste tube 25 is connected to one side of the coupling member 127, and a flow passage 124 is formed therein.

An end of the liquid feed tube 28 is connected to one side of the fitting hole 133 to communicate the flow passage therein with the flow passage 125.

The head body E uses the cleaning member 112 of a star shape in cross section having a through hole 132 as shown in FIG. 13.

A sleeve 121 is, for example, made of a resin material in a shape of a tube shorter than the cleaning member 112, and has two round holes 131 formed in the outer circumference thereof. Further, plural anchoring flanges 121a are provided on the outer periphery of the base end, the anchoring flanges 121a forming gaps t maintaining a distance in the circumferential direction and radially extending. At the front end of the sleeve 121 are further formed notches 121b facing each other.

The front end of the sleeve 121 is inserted in the through hole 132 of the cleaning member 112, and is pushed until the anchoring flanges 121a come in contact with the end face of the cleaning member 112. The cleaning member 112 is adhered to the outer peripheral surface of the sleeve 121 at a position at where the front end of the sleeve 121 has entered into the through hole 132 of the cleaning member 112 by 3 to 5 mm.

The waste pipe 122 is, for example, made of a resin material in a shape of a slender pipe having a diameter smaller than that of the sleeve 121, and forms a waste passage 114 therein, has its front end closed, and has a flange 122a formed along the outer circumference thereof. The waste pipe 122 has an outlet of the waste passage 114 on the base end side, has the outer periphery that is slightly narrowed at the edge of the base end 122b, and has a circumferential groove 122c formed in the outer periphery thereof near the base end 122b. Further, the flange 122a has positioning protuberances 122d formed facing each other and being directed toward the base end 122b, and plural waste ports 115 are formed in the outer periphery near the flange 122a. The positioning protuberances 122d are protruding by a length shorter than the length of the notches 121b of the sleeve 121.

The base end 122b of the waste pipe 122 is inserted in the sleeve 121 through the through hole 132 of the cleaning member 112, the positioning protuberances 122d are engaged with portions of the notches 121b, and the cleaning member 112 is detachably attached to the waste pipe 122 through the sleeve 121. The round holes 131 of the sleeve 121 are brought into agreement with the waste ports 115. Among the plural waste ports 115, the one closer to the flange 122a is partly communicated with the notches 121b of the sleeve 121.

The outer casing 123 is, for example, made of a flexible material such as a silicone, rubber or the like in a cylindrical shape having a diameter larger than that of the waste pipe 122, with its base end 123a being expanded like a skirt and forming a circumferential stepped portion 123c in the inner circumference thereof at an end 123b. As shown in FIG. 12, further, plural pushing protuberances 123d are formed on the inner periphery near the base end 123a maintaining a gap in the circumferential direction and slightly protruding toward the inner side.

The base end 122b of the waste pipe 122 is inserted through the opening at the end 123b of the outer casing 123, is further pushed to pass through the pushing protuberances 123d so as to protrude beyond the opening at the base end 123a, while the circumferential stepped portion 123c engages with the anchoring-flanges 121a of the sleeve 121 to thereby constitute the head body E. Then, the liquid feed passage 113 is formed between the outer casing 123 and the waste pipe 122, and the liquid feed ports 116 are formed among the plural gaps t of the anchoring flanges 121a.

Then, the head body E is coupled to the grip F to constitute the cleaning head 60. In this case, the base end 122b of the waste pipe 122 is inserted in the fitting hole 126 of the grip F and is inserted in the coupling member 127 to be abut with the annular protuberance 127a, and the front end 120a of the grip F is fitted in the base end 123a of the outer casing 123. The waste passage 114 and the liquid feed passage 113 of the head body E are communicated with the flow passages 124 and 125 of the grip F respectively. In coupling the head body E with the grip F, a click feeling is obtained when the base end 122b of the waste pipe 122 rides over the O-ring 128.

The front end 120*a* of the grip F is pressed by the resilience on the base end 123*a* of the outer casing 123, and a gap between the grip F and the outer casing 123 is air-tightly sealed together. Further, a gap between the waste pipe 122 and the grip F is air-tightly sealed together by the O-ring 128.

To wash the oral cavity, the water is fed into the liquid feed passage 113 from the flow passage 125 through the liquid feed tube 28 in the same manner as shown in, for example, FIG. 8, fed into the oral cavity from the liquid feed port 116 through the cleaning member 112, so that the oral cavity can be cleaned with the cleaning member 112 impregnated with the water. On the other hand, waste liquid and the like collected in the oral cavity is sucked into the waste passage 114 from the cleaning member 112 through the waste port 115 and is drained through the waste tube 25.

When it is desired to replace the cleaning member 112 that is worn out, the waste pipe 122 of the head body E is removed from the fitting hole 126 of the grip F and the base end 123*a* of the outer casing 123 is removed from the grip F.

Then, the waste pipe 122 is removed from the outer casing 123, the sleeve 121 is removed from the waste pipe 122, and the cleaning member 112 is replaced by a new one together with the sleeve 121.

INDUSTRIAL APPLICABILITY

As described above, the oral cavity cleaning device of the present invention is suited for cleaning the oral cavity with its cleaning head held by hand by a nursing person and introduced into the oral cavity of a person who is confined to the bed or of a physically disabled person while driving pump, thereby to suck and remove residual matter such as lees of foods remaining in the oral cavity, and to wash the oral cavity by blowing out a liquid such as water or pharmaceutical solution from the cleaning head while sucking and removing waste liquid after washing.

What is claimed is:

1. An oral cavity cleaning device, comprising:

a cleaning head having a liquid feed port and a waste port;

a liquid feed passage connected to the liquid feed port through which liquid is fed, via a pump, to the cleaning head and into the oral cavity via the liquid feed port to wash the oral cavity;

a waste passage connected to the waste port through which waste liquid in the oral cavity is sucked and drained by the cleaning head; and a cleaning member mounted on the cleaning head covering the liquid feed port and the waste port, the cleaning member being made of a porous material having a liquid-permeating property, wherein the cleaning member is substantially cylindrical in shape and has a hole for removably receiving the cleaning head.

2. An oral cavity cleaning device according to claim 1, wherein said cleaning head is provided with a waste pipe that forms the waste passage, and the end of said waste pipe is arranged in said cleaning member.

3. An oral cavity cleaning device according to claim 1, wherein the outer circumference of said cleaning member is formed rugged.

4. An oral cavity cleaning device according to claim 1, wherein a cleaning pump feeds the liquid to said cleaning member through said waste passage at the time of cleaning said cleaning member.

5. An oral cavity cleaning device according to claim 1, wherein said cleaning head is constituted by detachably attaching a grip to a head body, forming an outer member of said head body using an elastic material, and fitting an end of said grip to a base end of the outer member to air-tightly couple said grip and said outer member together.

* * * * *